US005589498A

United States Patent [19]
Mohr et al.

[11] Patent Number: 5,589,498
[45] Date of Patent: Dec. 31, 1996

[54] TRANSDERMAL DELIVERY OF THE ACTIVE ENANTIOMER OF KETOROLAC

[75] Inventors: Judy M. Mohr, Menlo Park; Richard W. Baker, Palo Alto; Lisa A. Nakaji, San Jose, all of Calif.

[73] Assignee: Pharmetrix Corporation, Menlo Park, Calif.

[21] Appl. No.: 470,648

[22] Filed: Jun. 6, 1995

Related U.S. Application Data

[63] Continuation of Ser. No. 8,814, Jan. 22, 1993, abandoned, which is a continuation of Ser. No. 973,801, Nov. 9, 1992, abandoned.

[51] Int. Cl.$^6$ ............................ A61K 31/40; A61K 9/70
[52] U.S. Cl. .......................................... 514/413; 424/449
[58] Field of Search .............................. 514/413; 424/449

[56] References Cited

U.S. PATENT DOCUMENTS

| | | | |
|---|---|---|---|
| 4,089,969 | 5/1978 | Muchowski et al. | 424/274 |
| 4,615,699 | 10/1986 | Gale et al. | 604/897 |
| 4,624,665 | 11/1986 | Nuwayser | 604/307 |
| 4,687,481 | 8/1987 | Nuwayser | 604/897 |
| 4,818,541 | 4/1989 | Sanderson | 424/448 |
| 4,898,734 | 1/1990 | Mathiowitz et al. | 424/426 |
| 4,910,205 | 3/1990 | Kogan et al. | 514/290 |
| 4,927,687 | 5/1990 | Nuwayser | 424/449 |
| 4,943,435 | 7/1990 | Baker et al. | 424/448 |
| 4,952,402 | 8/1990 | Sparks et al. | 424/419 |
| 4,992,445 | 2/1991 | Lawter et al. | 514/279 |
| 5,028,435 | 7/1991 | Katz et al. | 424/484 |
| 5,049,386 | 9/1991 | Eppstein et al. | 424/427 |
| 5,069,909 | 12/1991 | Sharma et al. | 424/449 |
| 5,091,182 | 2/1992 | Ong et al. | 424/400 |
| 5,114,946 | 5/1992 | Lawter et al. | 514/279 |
| 5,124,157 | 6/1992 | Colley et al. | 424/448 |
| 5,519,046 | 5/1996 | Noda et al. | 514/413 |

OTHER PUBLICATIONS

Gusman et al., *Chemical Abstracts* 104(15): 129734n, 1986.
Brocks et al., *Medline Abstract* No. 93092511, 1992.
Yu, et al., "Percutanteous Absorption of Nicardipine and Ketorolac in Rehsus Monkeys," *Pharmaceutical Research*, vol. 5, No. 7, 1988, pp. 457–462.
Greenwald, "Ketorolac: An Innovative Non–Steroidal Analgesic," *Drugs of Today*, vol. 28, No. 1, 1992, pp. 41–61.
Baker, R. W. *Controlled Release of Biologically Active Agents*, John Wiley & Sons, NY, pp. 4–10 (1987).
Jamali et al. *J. of Pharmaceutical Sciences* 789 695–714 (1989).
Campbell, D. B. *European J. of Drug Metabolism and Pharmacokinetics* 15 109–125 (1990).
Guzman, et al. *J. Med. Chem.* 29 589–591 (1986).
Mroszczak et al. *Clin. Pharmacology & Therapeutics* 49 126 (1991).
Stinson *C&EN* 46–79 (Sep. 28, 1992).
Rowland & Tozer *Clinical Pharmacokinetics: Concepts and Applications* 2nd Ed. (1989) pp. 19–25.
Drayer *Clinical Pharmacology & Therapeutics 40* No. 2 125 (1986).
Smith *Pharmacology & Toxicology* 65 321–331 (1989).
Ariens, et al. *Biochemical Pharmacology* 37 9–18 (1988).

*Primary Examiner*—Marianne M. Cintins
*Assistant Examiner*—William R. A. Jarvis
*Attorney, Agent, or Firm*—Townsend and Townsend and Crew

[57] ABSTRACT

The invention provides for the transdermal delivery of the active enantiomer of the analgesic ketorolac. Transdermal patches according to the invention are capable of delivering (–) ketorolac to a patient at therapeutically effective levels, at a flux rate of 20 µg/cm$^2$.hr or more. Patches for use in the present invention may be adhesive matrix, monolithic matrix, or liquid reservoir transdermal patches.

19 Claims, 3 Drawing Sheets

TRANSDERMAL DELIVERY OF THE ACTIVE ENANTIOMER OF KETOROLAC

CROSS-REFERENCES TO RELATED APPLICATIONS

This application is a continuation of Ser. No. 08/008,814, filed Jan. 22, 1993, now abandoned, which is a continuation of Ser. No. 07/973,801, filed 9 Nov. 1992, now abandoned, the contents of which are hereby expressly incorporated by reference.

BACKGROUND OF THE INVENTION

The present invention relates to a transdermal patch for administering ketorolac. More particularly, the invention concerns transdermal delivery of the active enantiomer of ketorolac from a patch that can deliver a therapeutically effective dose of (−) ketorolac through the skin of a patient in need of treatment with ketorolac for an extended period of time of at least 12 hours or more.

Ketorolac is a non-steroidal anti-inflammatory agent with potent analgesic properties. The drug is currently administered as the racemic mixture orally or by injection and is commercially available in forms suited for such modes of delivery. Ketorolac tromethamine salt in sterile water for intramuscular and intravenous administration is available at concentrations ranging from 1.5% (15 mg in 1 ml) to 3% (60 mg in 2 mls). Typically, when injected, a bolus dose of 30 to 60 mg is first given followed by subsequent injections of half the loading dose (15 to 30 mg) every 6 to 8 hours. The total daily doses of the drug as such is in the range of 60–120 mg. Delivered at these levels, the drug is extremely effective. However, the need for repeated injections due to the relatively rapid metabolism of the drug makes this mode of delivery inconvenient in certain situations.

A far more convenient and acceptable form of delivery is simple oral delivery 2 to 3 times per day. However, oral administration of ketorolac can be quite irritating to the gastrointestinal tract. Thus, for oral use, the FDA has approved only low-dosage tablets containing only 10 mg of ketorolac tromethamine salt. Of course patients can take more than one tablet, but in general it is normally not safely possible to maintain the same highly effective blood levels obtained with the injectable form when the drug is given orally.

Thus there is an interest in developing alternative modes of delivering ketorolac which do not have the gastrointestinal side effects produced by oral formulations but which are more convenient than injection methods. Nasal formulations of ketorolac are described in application U.S. Ser. No. 875,700, filed 29 Apr. 1992. In application U.S. Ser. No. 07/973,801 filed Nov. 9, 1992, now abandoned, the transdermal delivery of the active enantiomer of ketorolac is described.

The use of transdermal patches for drug delivery is particularly beneficial when it is desired to maintain a constant blood level of drug in the patient for extended periods of time. There is an added benefit in that oftentimes, the required dose of a drug when delivered by a 24 hour transdermal patch can be one half or less that of the dose delivered by a single once a day intravenous or oral dose. This is particularly true if the drug has a high clearance value. With conventional drug delivery methods, if a drug has a high clearance value it is necessary to administer a large dose of the drug to extend the time it takes to blood drug levels to fall below the therapeutically effective level. But with transdermal delivery, the dose of a drug with a high clearance value can be lower since the drug is controlled released, and does not have to be administered at levels much greater than the therapeutically effective level.

The concept of clearance is described in detail in Rowland & Tozer's, *Clinical Pharmacokinetics: Concepts and Applications*, (2nd Ed. 1989) [hereinafter Rowland & Tozer]. Briefly, clearance does not indicate how much drug is being removed from the system but, rather, the volume of biological fluid such as blood or plasma that would have to be completely freed of drug to account for the elimination. Clearance is expressed as a volume per unit of time. Clearance by means of various organs of elimination is additive. Elimination of drug may occur as a result of processes that occur in the kidney, liver, and other organs. When the respective clearance by each organ is added together, they equal total systemic clearance.

The half-life of a drug is the amount of time it takes the total level of drug in a body to decrease by 50%. Clearance is related to the half-life of a drug by Equation 1:

$$T_{1/2} = \frac{0.693 \times \text{Volume of distribution}}{\text{Clearance}}$$

Figure 1:
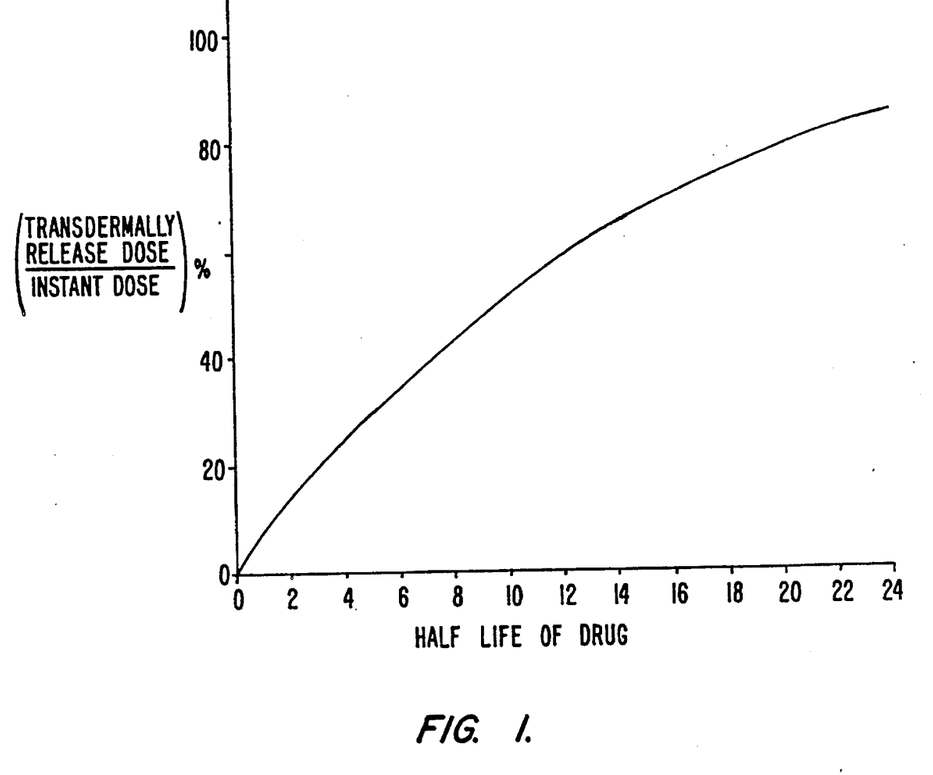
FIG. 1 compares the ratio of drug delivered transdermally (controlled release) to the drug delivered as an instant dose (drug injection) required to achieve 24 hour therapy as a function of the half-life of the drug.

The relationship between the conventional dose of a drug and the dose of drug delivered transdermally can be calculated if the half-life of the drug is known. This procedure is described on pages 5–10 of Baker, R. W., *Controlled Release of Biologically Active Agents*, John Wiley and Sons, New York, (1987) [hereinafter Baker]. Using this procedure, the data shown in Table I and FIG. 1 has been calculated.

Table I shows that the ratio of dose required for the transdermal delivery of a drug compared to the dose required for conventional drug delivery decreases as the half-life of the drug decreases. Thus, if the half-life of the drug is 24 hours, then a transdermal patch delivering drug to the body at a relatively constant rate should only have to deliver 84.5% of the dose of a conventional instant dose form of the drug delivered once every 24 hours. In this case, the advantage offered by controlled transdermal delivery is relatively small, only a 15.5% reduction in dose. However, if the half-life of the drug is 4 hours, the approximate half-life of ketorolac, then the advantage offered by constant delivery is much greater compared to conventional delivery given once every 24 hours, namely a reduction in dose of almost 75%. Even if an injectable dose is given every 8 hours, the reduction in dose obtained when a transdermal patch is used is still substantial, being on the order of 40 to 50%.

TABLE I

| Drug Half-life (in hours) | Ratio of dose required of controlled release form compared to conventional form (for a 24-hour device) |
|---|---|
| 24 | 0.845 |
| 12 | 0.595 |
| 6 | 0.350 |
| 4 | 0.250 |
| 3 | 0.205 |

Thus it follows that if the total amount of ketorolac delivered by regular injections three times a day to control pain is approximately 60–120 mg/day, then a 30–60 mg/day dose delivered transdermally would produce approximately the same benefit without the problems of overdosing and underdosing associated with injectable delivery. This type of calculation has led to interest in delivering ketorolac transdermally. For example, transdermal delivery of ketorolac from nearly saturated solutions in various enhancer combinations has been studied by others (D. Yu et al, *Pharm. Res.* 5(7): 457–462, (1988)). In another study, a 2% ketorolac topical gel was studied (R. Greenwald, *Drugs of Today,* 29(1): p.52, (1992)). The patients applied 3 g of the gel three times per day without occlusion. Serum concentrations of approximately 0.17–0.18 µg/ml were attained, significantly below the generally accepted target level for good analgesia with ketorolac of 0.3 to 5.0 µg/ml.

Figure 2:
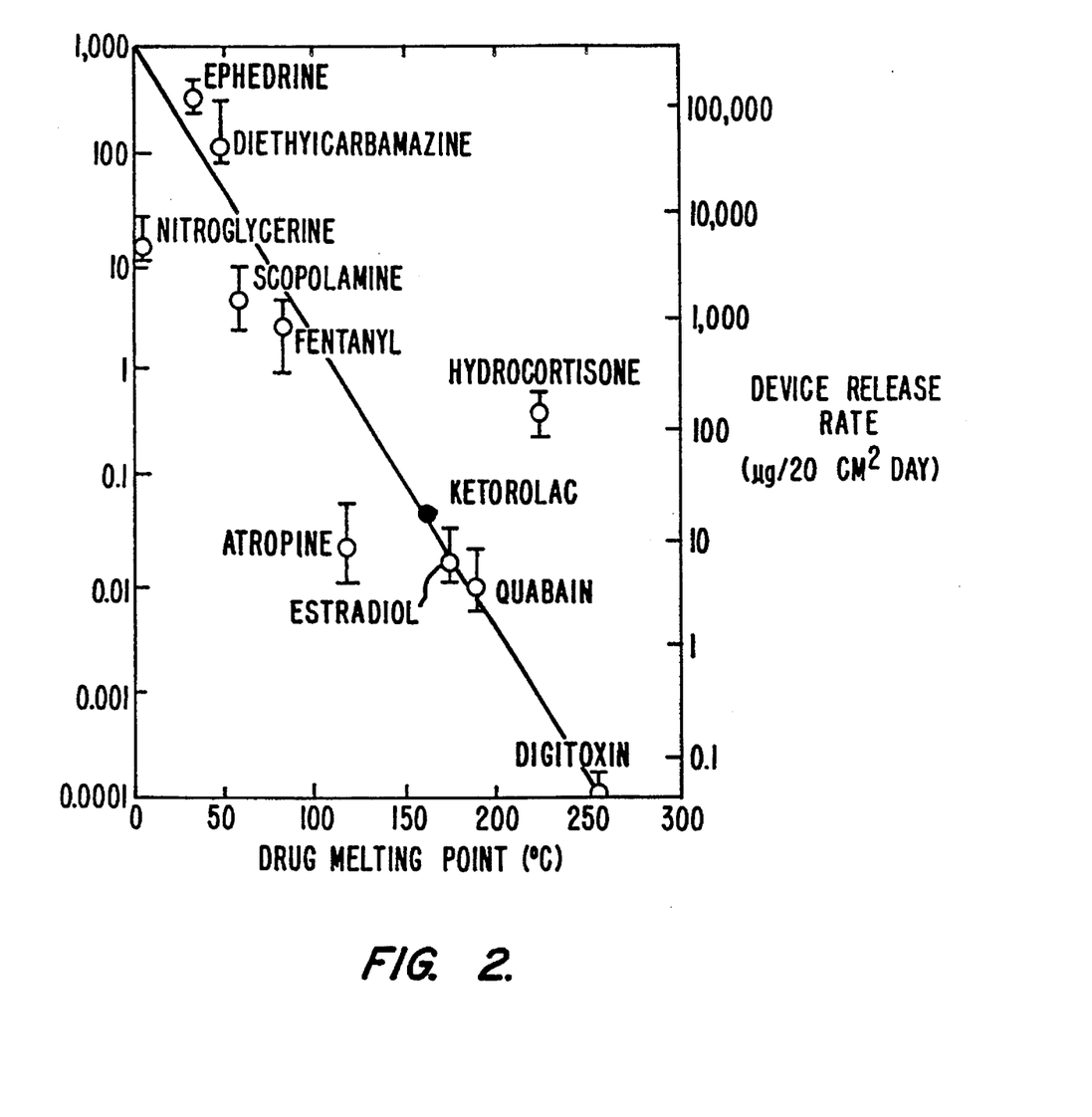
FIG. 2 shows the relationship between the flux rate of various drugs and their melting points.

These dissatisfying results are not surprising. It is well known in the art of transdermal drug delivery that it is very difficult to deliver drugs at a rate of greater than 10–20 µg/cm$^2$.hr. Of the 9 drugs delivered by approved commercial transdermal formulations only two, nicotine and nitroglycerine, both very permeable liquids, deliver drug at this rate. Most of the other formulations deliver the drugs at a much lower rate. It has been proposed that the permeability of skin to a given drug can be correlated with the drug's melting point according to the relationship set forth in FIG. 2 (Baker, supra). Based on this, the expected flux of ketorolac with a melting point of 160° C. would be 0.06 µg/cm$^2$.hr. The expected flux of ketorolac tromethamine, which has melting point similar to that of the free acid, would be about the same.

It follows that if the required transdermal dose of 30–60 mg/day of ketorolac is to be delivered by a transdermal device, the area of the patch required would be impossibly large, on the order of 2–4 m$^2$. Of course, skin permeation enhancers could be used to increase the delivery, but if conventional sized patches of the order of 30 cm$^2$ or less are to be used, skin permeation rates from the patch of the order of 42–84 µg/cm$^2$.hr would be required—a very considerable degree of enhancement.

Accordingly, it is an object of this invention to provide a transdermal patch that can deliver ketorolac at a rate that attains a therapeutic level.

Another object of the present invention is to provide a ketorolac transdermal patch that is less than 30 cm$^2$ in active surface area.

It is a further object of the invention to provide a transdermal ketorolac patch that avoids or minimizes skin irritation.

Another object of the invention is to provide a ketorolac transdermal patch that is effective in providing analgesia for periods of 12 hours or more.

These and other objects and features of the invention will be apparent to those skilled in the art from the following detailed description and appended claims when taken in conjunction with the figures.

SUMMARY OF THE INVENTION

A patch for the transdermal administration of ketorolac is described. The patch is capable of delivering therapeutically effective levels of ketorolac through a patient's skin for a period of 12 hours or more. The patch comprises an occlusive backing layer in contact with a drug depot containing (−) ketorolac and an enhancer, and is capable of delivering (−) ketorolac through a patient's skin at flux rates of about 20 µg/cm$^2$.hr or more.

In one embodiment of the invention, the transdermal patch is an adhesive matrix type wherein the drug depot is an adhesive polymer in which the (−) ketorolac and enhancer are dispersed.

In another embodiment of the invention, the transdermal patch is a reservoir type whereby the drug depot is defined by the backing layer and a porous membrane which are sealed together at their peripheral edges.

In another embodiment of the present invention, the transdermal patch is a monolithic matrix type wherein the drug depot is a polymer matrix in which the (−) ketorolac and enhancer are dispersed. A porous membrane covers the depot at its skin-facing side, and an adhesive layer covers the skin-facing side of the membrane.

A method of administering ketorolac is also described. The method comprises applying a transdermal patch to the skin of a patient in need of ketorolac, said patch containing (−) ketorolac and an enhancer and delivering (−) ketorolac through the patient's skin at a flux rate of about 20 µg/cm$^2$.hr or more.

DESCRIPTION OF THE PREFERRED EMBODIMENTS

In describing and claiming the present invention, the term "ketorolac" as used herein refers to any therapeutic form of the analgesic ketorolac including the free acid and its pharmaceutically effective salts, such as hydrochloride, mesylate, hydrobromide, tromethamine, and the like.

The term "(−) ketorolac" as used herein refers to the active enantiomer of ketorolac free acid and its pharmaceutically effective salts, the active enantiomer being substantially free of the inactive enantiomer.

The term "racemic ketorolac" as used herein refers to the active and inactive enantiomers (or the racemate) of ketorolac free acid in combination and their pharmaceutically effective salts.

To date, it has been difficult to transdermally deliver a therapeutically effective dose of ketorolac. This is due primarily to the low flux of ketorolac and the large dose required to attain therapeutic blood levels. The applicants however, have discovered that (−) ketorolac is as permeable to human skin as the racemate. This is an important result because the great majority of the pharmaceutical effect of ketorolac is due to the (−) enantiomer of ketorolac while the (+) enantiomer is relatively ineffective. The use of the (−) enantiomer rather than a racemic mixture thus reduces the amount of drug delivered transdermally that is required to equal the therapeutic effect of the conventional bolus formulation. As described above, approximately 30 to 60 mg/day of the racemic mixture of ketorolac is required to achieve the same therapeutic effect as the bolus injectable dose. The transdermal dose of the racemic mixture requires a delivery rate of about 40 to 80 µg/cm$^2$.hr for a conventional 30 cm$^2$ patch. However, transdermal delivery of the (−) enantiomer reduces the required daily dose to 15–30 mg/day or even less. Thus, the required transdermal delivery rate is reduced to 20–40 µg/cm$^2$.hr from a 30 cm$^2$ patch.

The ketorolac transdermal patch formulations of the present invention result in a skin flux rate of at least 20 µg/cm$^2$.hr. Thus, the patches of the present invention are therapeutically useful at active surface areas of less than 30 cm$^2$. As used herein, the term "active surface area" refers to the area of the patch where drug is transmitted to the skin. Accordingly inactive surface area may, for example, be peripheral to the active surface area and may provide an adhesive or structural function.

Ketorolac tromethamine is freely soluble in water and methanol. It has a pKa of 3.54 and a molecular weight of 376.41. The compound is an off-white, crystalline material that melts between 160° C. and 170° C. As such, it is a relatively difficult drug to deliver transdermally because of the extremely lipophilic barrier of the stratum corneum. For adequate skin penetration rates, a chemical enhancer is necessary. There are numerous possible penetration enhancers that can be used such as solvent-type and plasticizing-type enhancers. As used herein, the term "enhancer" is meant to encompass any enhancer or combination of enhancers that increases the permeability of ketorolac to the stratum corneum.

As used herein, "plasticizing-type enhancer" refers to fatty acids and fatty alcohols that are capable of increasing the permeability of drugs to the stratum corneum. A preferred group of plasticizing-type enhancers are fatty acid esters and similar hydrophobic compounds generally having a molecular weight of greater than 150 but less than 300 and having a water solubility of less than 0.5 wt % and preferably 0.2 wt % or less. Without limiting the scope of the present invention, the following is proposed as the mechanism of action of plasticizing-type enhancers. It is believed that the function of these plasticizing enhancers is to migrate into the upper stratum corneum layers of the skin and to remain there for a prolonged period of time. The stratum corneum layer, although only 25–50 microns thick, is the principal barrier to transdermal permeation. The plasticizing enhancers that migrate into the skin serve to increase the mobility and solubility of ketorolac into the skin. To be effective as a plasticizing enhancer, the molecule should be relatively large. In general a molecular weight of approximately 150 is required, or greater than 10 carbon atoms. The plasticizing enhancer must also be relatively water insoluble or it will leach into the subcutaneous tissue layers below the stratum corneum. Thus, plasticizing enhancers with water solubility of less than 0.5 wt % are preferred. It is also preferred that the molecular weight of the plasticizing enhancer be less than 500, because molecules larger than this will have difficulty migrating into the stratum corneum layers.

Fatty alcohols that can be used as plasticizing enhancers include stearyl alcohol and oleyl alcohol. Fatty acids that can be used include oleic acid, lauric acid, myristic acid, palmitic acid, stearic acid, linoleic acid, and palmitoleic acid. Fatty acid esters containing more than 10 to 12 carbons can also be used such as isopropyl myristate and the methyl and ethyl esters of oleic and lauric acid. But many other compounds can also be used such as diethyl hexyl phthalate, octyldodecyl myristate, isostearyl isostearate, caprylic/capric triglyceride, glyceryl oleate, and various oils, such as wintergreen or eucalyptol. Despite these teachings, simple plasticizing enhancers do not sufficiently increase the skin penetration rate of ketorolac to the level required to achieve a therapeutic effect.

As used herein, "solvent-type enhancer" refers to alcohols having molecular weights less than 150 that are capable of increasing the permeability of drugs to the stratum corneum. Solvent type enhancers, which include ethanol, propanol, butanol, benzyl alcohol, glycerin, and propylene glycol, are often better enhancers because they generally provide higher flux rates than plasticizing enhancers. These compounds are all relatively low molecular weight, generally less than 150 in molecular weight. Preferred solvent enhancers have a molecular weight of less than 100. They are also relatively hydrophilic, generally being greater than 2 wt % soluble in water, and are preferably greater than 10 wt % soluble in water. Most preferred solvent enhancers are completely water miscible. While these solvent enhancers can be useful in delivering ketorolac through the skin when used alone, large amounts must be applied continuously to get a prolonged therapeutic effect. As such, they are often irritating to the skin. For example, a 60% aqueous solution of the solvent-type enhancer ethanol is extremely irritating to most patients. For most patients, a 40% aqueous solution is generally acceptable. Unfortunately a 40% solution of ethanol is not a sufficiently powerful enhancer for ketorolac. When a plasticizing type enhancer is used in combination with a solvent type enhancer it is possible to deliver ketorolac through the stratum corneum at therapeutically effective levels. Such a mixture achieves high delivery rates of the drug with relatively dilute solutions of the solvent enhancer. This eliminates the irritation that occurs when solvent-type enhancers solutions are used alone at high concentrations without plasticizing enhancers. When used with plasticizing type enhancers, the function of the solvent enhancer is to rapidly diffuse into the stratum corneum layer of the skin making it possible for the heavier, less mobile plasticizing enhancer to enter the stratum corneum layer. The small size and hydrophilic nature of these solvent enhancers makes them very effective in this role. However, these molecules tend to migrate through the stratum corneum layers and into the subcutaneous tissues very quickly.

There are several designs of transdermal patches that are commonly used as shown in FIGS. 3–6, and discussed in more detail below. The particular patch design selected is determined based on a number of factors, one of the more important being the enhancer system. The simplest type of transdermal patch is the adhesive matrix patch where the drug and the enhancer are formulated into the skin adhesive layer. The adhesive layer serves both as the drug and enhancer reservoir as well as the adhesive layer which attaches the patch to the patient's skin. Adhesives by nature are lipophilic being comprised of long chain hydrocarbons. This allows for incorporation of most plasticizing type enhancers which are also typically lipophilic. On the other hand, many of the hydrophilic solvent type enhancers are not compatible with the adhesives. Because high flux rates of solvent enhancer (on the order of 0.1 mg/cm$^2$.hr or more) are required to achieve therapeutically effective flux rates of ketorolac, it is necessary to formulate patches having in the range of 50–100 mg of the solvent enhancer. Only a limited number of the hydrophilic solvent type enhancers typically used for transdermal patches can be formulated at these levels into an adhesive matrix. Solvent type enhancers which can be formulated into an adhesive matrix generally have a boiling point of greater than 100° C. Once such enhancer, propylene glycol, is a preferred solvent type enhancer for the adhesive matrix patch embodiment of the present invention.

When solvents having a boiling point of less than 100° C. are selected, the transdermal patch will generally be a monolithic matrix type or a reservoir type. These designs are discussed in further detail below. The matrix in these patches can be made from more hydrophilic materials in which the load of solvent enhancer can be contained along with the drug.

In general, the total amount of plasticizing enhancer will be less than the solvent enhancer. For example, a ratio of 1 part plasticizing enhancer to at least 10 parts solvent enhancer is preferred and more preferred is 1 part to 20 or greater parts solvent enhancer. A preferred combination for a reservoir-type device, described in detail below, is 20–60% of a C2–C4 alcohol enhancer, 0.5–20% of a plasticizing type fatty acid ester with the balance being water, glycerine, or propylene glycol. A most preferred combination for a reservoir device is 30–45% ethanol, and 1–5% isopropyl myristate with the balance being water. Ethanol in combination with isopropyl myristate at pH 7 is capable of increasing the skin penetration rate of ketorolac to therapeutically effective levels. This combination is advantageous because the use of a non-acidic enhancer formulation reduces irritation.

Patch Design

Figure 3:
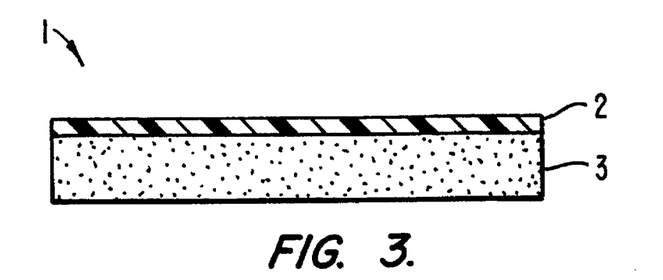
FIG. 3 shows an adhesive matrix transdermal patch having an impermeable backing and an analgesic-containing adhesive polymer matrix.
Figure 4:
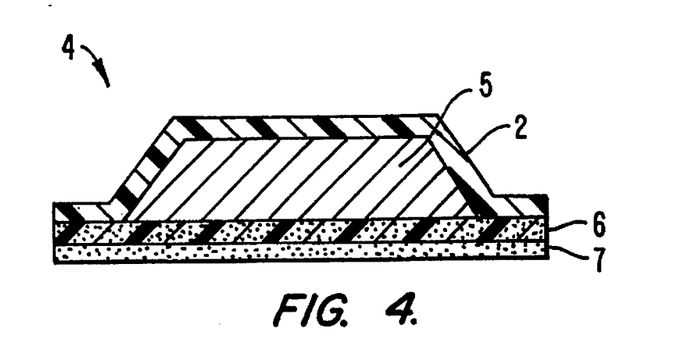
FIG. 4 shows a reservoir type transdermal patch having an impermeable backing, a drug depot, a porous membrane, and an adhesive layer. The backing and the porous membrane are sealed at their peripheral edges, thus defining the drug depot.
Figure 5:
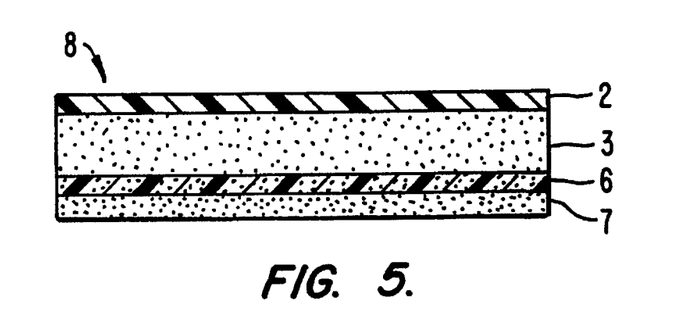
FIG. 5 shows a monolithic matrix transdermal patch having an impermeable backing, a drug depot comprising a polymer matrix in which drug is dispersed, an optional porous membrane, and an adhesive layer.

Several types of transdermal patches can be used for the delivery of ketorolac as shown in FIGS. 3, 4 and 5. The simplest patch design is an adhesive matrix type and consists only of a backing material at the skin-distal side of the patch and a drug depot layer comprised of enhancer, drug, and adhesive which attaches directly to a patient's skin. In this patch it is possible to incorporate the lipophilic plasticizing type enhancers, such as the fatty acid ester isopropyl myristate. Some solvent enhancers with long carbon chains will also work. In Example 2 the use of propylene glycol, a solvent type enhancer, and isopropyl myristate is shown in a simple adhesive matrix type patch.

Another type of transdermal patch is a monolithic matrix type where a material other than the adhesive serves as the drug depot. For these patches, hydrogel materials may be used such as polyurethane, gelatin, and pectin. Such materials can contain relatively large volumes of solvent type enhancer necessary for effective drug delivery. At the skin-facing side of the drug depot is a porous membrane layer, for example, a non-woven polyester membrane. The patch is attached to a patient's skin via an adhesive layer which is located at the skin-facing side of the membrane layer. The adhesive layer may cover the entire skin-facing side of the membrane, or may be located at the periphery of the membrane. Drug flux rates may be improved by placing plasticizing enhancer in the adhesive layer. These types of patches are disclosed in Examples 5, 6, and 7.

The third type of patch is the liquid reservoir system and is used when very large amounts of solvent type enhancers are required. This is the case in Example 8 where the two primary components of the formulation are ethanol and water. The patch comprises a backing layer and a porous membrane which are heat-sealed at their periphery to define a drug-depot.

A basic embodiment of the present invention is shown in FIG. 3. Referring now to this figure, the ketorolac adhesive matrix type transdermal patch, 1, comprises an impermeable backing layer, 2, and an adhesive matrix layer, 3, which serves both as a depot for ketorolac and a means of adhering the device to the skin.

The impermeable backing layer, 2, defines the non-skin facing side of the patch in use. The functions of the backing layer are to provide an occlusive layer that prevents loss of ketorolac and the enhancers, in particular the solvent enhancer, to the environment and to protect the patch. The material chosen should exhibit minimal ketorolac and enhancer permeability. The backing layer should be opaque because ketorolac degrades in the presence of light. Ideally, the backing material should be capable of forming a support onto which the ketorolac containing mixture can be cast and to which it will bond securely. A preferred material is polyester or aluminized polyester. Preferred backings are polyester medical films available for example from 3M Corporation such as Scotchpak® 1005 or 1109. As an alternative to casting the matrix directly on the backing, the polymer matrix may be cast separately and later stuck to the backing material.

The ketorolac adhesive matrix layer, 3, comprises ketorolac dispersed in an adhesive polymer matrix. As used herein, the term "dispersed" refers to the distribution of ketorolac throughout the matrix. The drug may be dispersed in a dissolved and/or undissolved state, but is preferably dissolved. The monolith layer may be prepared as follows. First a solution of the adhesive polymer is obtained or prepared. Another solution of ketorolac in appropriately selected enhancers is prepared and mixed until the drug is dissolved or evenly dispersed. The ketorolac/enhancer solution is then added to the adhesive polymer solution and the mixture is homogenized. The solution may be poured into a mold or cast alone or on the desired backing material. The casting is then left for the solvent to evaporate at room temperature or in an oven at a slightly elevated temperature. After solvent evaporation, the adhesive matrix takes the form of an adhesive polymer film typically having a thickness in the range of about 50 to 100 μm.

It will be appreciated that for a given desired total ketorolac load the percentage of loading may be varied by varying the adhesive matrix thickness. The total ketorolac content of the adhesive matrix will be sufficient to provide a one day dosage of ketorolac. Also the amount of ketorolac in the adhesive matrix may exceed the delivered load to keep the concentration gradient high so that the flux-rate of the patch remains constant throughout its intended use. For example, in a patch designed to deliver a total of 30 mg of ketorolac over a 24 hour period and then to be replaced by a fresh patch as much as 50 to 100 mg of ketorolac may be included in the patch. This ensures high activity of ketorolac at the end of the 24 hour period. For similar reasons excess plasticizing and solvent enhancers may also be included in the patch formulation.

The adhesive used in an adhesive matrix type patch can be selected from a variety of adhesives available commercially and known to those in the art. For example, common adhesives are those based on poly isobutylene, acrylic, and silicone. The selection of the adhesive is critical to realize a functioning adhesive matrix type transdermal patch. The enhancers and the drug are loaded directly into the adhesive and so the adhesive must retain its functioning properties in the presence of these additives. These adhesive properties include sufficient tack for good instantaneous adhesion to the skin as well as maintenance of adhesion. Often adhesives become stringy and gooey in the presence of the skin permeation enhancers leading to cohesive failure and residual adhesive left on the patient's skin after removal of the patch. In some cases, the patch looses adhesion altogether and falls off. The loss of tack and other adhesion properties generally dictates and limits the amount and type of enhancers that can be loaded into the adhesive matrix type patches. Some acrylate based adhesives, such as those available from Avery and National Starch and Chemical Company, are able to withstand relatively high loadings of enhancers, both solvent-type and plasticizing type.

Another embodiment of the present invention is a reservoir type transdermal patch shown in FIG. 4. Referring now to this figure, the ketorolac dispensing patch, 4, comprises, from skin-distal side to skin-facing side of patch, an impermeable backing layer, 2, a ketorolac reservoir (drug depot), 5, a porous membrane, 6, and an adhesive layer 7. The backing layer may be the same as that described for the adhesive matrix type patch above. The reservoir may take various forms, for example, the ketorolac may be dissolved in an enhancer or combination of enhancers, gelled or ungelled. Alternatively, the drug/enhancer mixture may be conveniently contained in the pores of a pad or foam material such as a polyurethane foam. The function of the reservoir is to keep the drug and enhancer(s) in good contact with the membrane layer.

The membrane layer, 6, in its most simple function provides mechanical support for the adhesive layer, 7. The membrane layer and backing layer are sealed at their peripheral edges to form the drug reservoir which contains a solution or gel of the solvent enhancer and drug with plasticizing enhancer. As used herein, the term "peripheral edges" of the membrane and backing layers refers to the areas that are sealed together to define the drug reservoir. Therefore, extraneous membrane and backing layer material may extend outwardly from the drug reservoir and peripheral edge. The membrane and adhesive layers must be freely permeable to ketorolac and to the enhancers. As such, the membrane layer should offer minimal diffusional resistance.

The nature of the membrane layer separating the reservoir from the skin is important. In vitro dissolution tests reveal that microporous polyethylene, which is commonly used as the membrane in transdermal devices, releases the contents of a solvent-containing reservoir at a rate far higher than the skin's ability to absorb. Preferably, the solvent should be in contact with the skin at the concentration level of the reservoir. Because microporous polyethylene has pores in the range of 0.2 to 0.5 microns in diameter one would expect that it would allow adequate flux of the solvent enhancer (being considerably smaller than 0.2 microns). However, when tested on skin, the flux of the solvent enhancer released from the microporous material is impeded. A more suitable membrane material for the transdermal patches of the present invention has pores greater than about 3 microns, for example, non-woven polyester (available from Dexter Corp., Windsor Locks, Conn.). The improved results provided from this material may be due to a convective wicking action of the polyester fabric which has pores in the range of 3–10 microns or more.

A preferred embodiment of the invention is a monolithic matrix type transdermal patch which is shown in FIG. 5. Referring now to this figure, the ketorolac dispensing patch, 8 comprises an impermeable backing layer, 2, a monolithic matrix layer, 3, an optional porous membrane layer, 6, and an adhesive layer, 7. The backing, membrane, and adhesive layers are selected as described above for the embodiments of FIGS. 3 and 4. The porous membrane provides structural support for the adhesive layer which simplifies the manufacturing of the device. The monolithic matrix layer is distinguished from the adhesive matrix of FIG. 3 where the monolith serves both as the drug reservoir and the skin adhesive.

Figure 6:
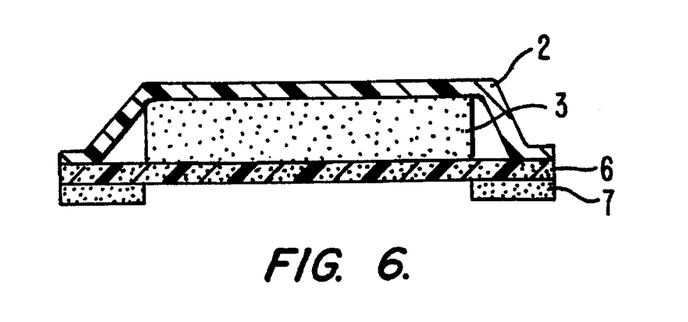
FIG. 6 shows a transdermal patch having an impermeable backing, a monolithic analgesic-containing matrix, a porous membrane, and a peripheral adhesive layer that is in contact with a non-active surface area.

In some instances, as shown in FIG. 6, the adhesive layer 7, may be applied to the periphery of the patch so as not to come in contact with solvent enhancers. This is particularly desirable in situations where a high loading of solvent type enhancers may interfere with adhesion.

Preferred monolith matrix materials are those capable of holding a large volume of liquids, such as water and the chemical enhancers employed. Suitable materials are various polymers such as hydroxy ethyl methacrylate (HEMA) ethyl methacrylate (EMA) blends, polyvinyl alcohols, polyvinyl pyrrolidine, gelatin, pectin, and other hydrophilic materials. Microporous particles may be incorporated into the polymer monolith to hold the solvent type enhancers used. The use of microporous particles in transdermal patches is disclosed by Katz et al. in U.S. Pat. No. 5,028,535, Sparks et al. in U.S. Pat. No. 4,952,402, and Nuwayser et al. in U.S. Pat. No. 4,927,687, all of which are hereby expressly incorporated by reference.

Ketorolac and enhancers may be loaded into the microporous particles before incorporation into the hydrophilic polymer. The particles are then evenly dispersed throughout the matrix by mixing. At high loadings of particles, the release of drug and enhancer is enhanced due to the formation of channels in the polymer matrix. Suitable microporous particles are diatomaceous earth, silica, cellulose acetate fibers from Hoechst Celanese, and Polytrap® from Dow Corning.

The solvent type enhancers used in a monolithic matrix or liquid reservoir transdermal patch are typically located in the drug reservoir. This is because of the hydrophilic nature of the solvent type enhancer which is generally present in relatively high proportions.

The hydrophilicity makes it incompatible in the lipophilic adhesive layer so that incorporation of the enhancer system solely into the adhesive is difficult. The plasticizing enhancer used is more hydrophobic in nature and is more compatible with the adhesive. In one embodiment of both the reservoir and monolithic type patches, the plasticizing enhancer is located in the drug depot with the solvent enhancer and drug. In another embodiment, the plasticizing enhancer is incorporated into the adhesive layer while the solvent type enhancer and drug are located in the drug depot. Placement of the plasticizing type enhancer in the adhesive is often desirable because it puts the enhancer in direct contact with the stratum corneum. The solvent enhancer in the drug depot above the adhesive sweeps through the adhesive layer carrying the plasticizing enhancer with it into the skin. In some cases the plasticizing type enhancer is loaded into the adhesive as well as into the drug reservoir.

The invention is now further illustrated by Examples 1 to 7 which are exemplary but not scope-limiting. While the examples were performed using racemic ketorolac, they are applicable to the use of (−) ketorolac because (−) ketorolac and the racemic mixture have similar flux and solubility characteristics as described above.

Measurement of skin permeation rates

EXAMPLE 1

Skin permeation rates of various ketorolac/enhancer formulations were determined using flow through diffusion cells with an active area of 1 $cm^2$ and a receiving volume of 3 ml. The receptor fluid, isotonic saline, was pumped into and through the cells by a peristaltic pump. Samples were collected in glass vials arranged in an automatic fraction collector. Human skin was placed on the lower half of the diffusion cell with the stratum corneum facing the donor compartment. The test solution or transdermal device was placed on the stratum corneum and the amount of drug permeated across the skin ($\mu g/cm^2$.hr) was calculated from the cumulative release.

Preparation of ketorolac adhesive matrix patches

EXAMPLE 2

Transdermal patches with 10% ketorolac were prepared by the following procedure. Ketorolac, 0.5 g, was dissolved in 0.21 g of propylene glycol and 0.21 g of isopropyl myristate. This mixture was added to 12.5 g of a pressure sensitive acrylate adhesive solution (DT 9852 by National Starch, 34% solids content). The solution was left to mix for 12 hours on a rolling mill. The drug-enhancer-adhesive mixture was then cast on Scotchpak X-21220 polyester backing with a 1000 µm casting knife. The solvent in the adhesive solution was evaporated at room temperature for 30 minutes and then in an oven at 100° for 15 minutes. The resulting adhesive film was laminated to a siliconized release liner (3M #1022). The resulting transdermal laminate was cut into disks 5 $cm^2$ for in vitro evaluation.

The average flux of ketorolac from this patch with 10% ketorolac, 8% enhancer (propylene glycol/isopropyl myristate), and 82% adhesive solids was 21.6±3.59 $\mu g/cm^2$.hr. The average cumulative amount of ketorolac released after 24 hours from these systems was 461.7±83.8 $\mu g/cm^2$.

EXAMPLE 3

Patches were prepared according to the mixing and casting procedure of Example 2 except with the following amounts of components: 0.5 g of ketorolac, 0.25 g of propylene glycol, 0.25 g of isopropyl myristate, and 11.7 g of acrylate adhesive 34 wt % solution.

An in vitro skin flux experiment was conducted following the methods of Example 1. The average flux of ketorolac from this patch with 10% ketorolac, 10% enhancer, and 80% adhesive solids was 21.66±3.07 $\mu g/cm^2$.hr. The average cumulative amount of ketorolac released after 24 hours from these systems was 324.26±88.63 $\mu g/cm^2$.

EXAMPLE 4

Patches were prepared according to the mixing and casting procedure of Example 2 except with the following amounts of components: 0.5 g of ketorolac, 0.30 g of propylene glycol, 0.30 g of isopropyl myristate, and 11.4 g of acrylate adhesive 34 wt % solution.

An in vitro skin flux experiment was conducted following the methods of Example 1. The average flux of ketorolac from this patch with 10% ketorolac, 12% enhancer, and 78% adhesive solids was 36.56±5.35 $\mu g/cm^2$.hr. The average cumulative amount of ketorolac released after 24 hours from these systems was 547.44±77.23 $\mu g/cm^2$.

Preparation of ketorolac monolithic patches

EXAMPLE 5

Monolithic ketorolac transdermal patches are prepared as follows. A solution of 44% ethanol, 22% glycerine, 22% propylene glycol and 12% ketorolac tromethamine is prepared. 11.5 g of the polyurethane prepolymer Hypol 5000 (WR Grace) is weighed into a plastic beaker. 5.0 g each of the above enhancer drug mixture and of Superfloss Diatomaceous Earth (Celite Corporation) is added to the Hypol 5000. After mixing well, the paste is cast between two sheets of siliconized polyester to a thickness of 540 µm on a double roll coater. The matrix is left overnight at room temperature to cure. After curing, a laminate of non-woven polyester and acrylate adhesive loaded with 30% isopropyl myristate is adhered to the matrix. Disks 5 $cm^2$ are cut from the matrix, and one side of the siliconized release liner is removed. The exposed matrix is placed on a sample of human skin and the permeation of ketorolac tromethamine is measured as described in Example 1.

EXAMPLE 6

A hydrogel-like ketorolac tromethamine transdermal matrix is prepared as follows. 3.0 g of glycerine and 7 g of deionized water are weighed into a beaker and mixed. 2.0 g of ketorolac tromethamine is added and mixed until dissolved. 10.0 g of 2-acrylamido-2-methylpropanesulfonic acid (AMPS, Lubrizol Corporation) is added and mixed. The mixture is purged with argon for 10 minutes while stirring. Then 0.5 g of 0.15% aqueous hydrogen peroxide is added and the prepolymer is cast onto Scotchpak X-21220 polyester backing. The prepolymer is cured in the oven at 45° C. for 2 hours. After curing, the matrix is rehydrated in the presence of isopropanol, water, and ketorolac tromethamine (44:44:12). Disks 5 $cm^2$ are cut from the rehydrated matrix, and the permeation of ketorolac tromethamine is measured as described in Example 1.

EXAMPLE 7

Monolithic matrix ketorolac transdermal patches were prepared as follows. In a first container, ethanol (0.83 ml), deionized water (6.6 ml), glycerine (1.6 ml), and pectin (0.83 g) were mixed together and set aside.

In a second container, 83 mg of potassium chloride was added to 1.66 ml of deionized water, mixed and set aside. In a third container, 1.3 g of ketorolac tromethamine was added to 6.6 ml of ethanol and mixed well. In a fourth container, gelatin (5 g), deionized water (5 ml) and glycerine (5 ml) were added together, mixed, and heated to 90° C. with constant stirring. The melted gelatin mixture was added to the pectin component in the first container and mixed. The aqueous potassium chloride was then added, mixed, and then the ketorolac solution was added and mixed. The formulation resulted in a slightly viscous solution that was light amber in color. The solution was then cast onto a transdermal backing material. A laminate of adhesive film loaded with 30% isopropyl myristate and non-woven polyester (Dexter 9770) is placed over the matrix as it is cooling. As the matrix cools, it solidifies adhering the non-woven polyester/adhesive laminate to it.

The matrix was placed on stratum corneum and the release of ketorolac was measured according to Example 1. The average flux was 24.9±0.2 $\mu g/cm^2$.hr. The average cumulative amount of ketorolac released after 24 hours from these systems was 555.2±187.8 $\mu g/cm^2$.

Preparation of ketorolac reservoir patches

EXAMPLE 8

An acrylate adhesive casting solution is prepared containing 30% isopropyl myristate. The casting solution is cast onto a polyester film (3M #1022) with a 750 µm knife and dried at room temperature for 30 minutes and then at 100° C. for 15 minutes. A non-woven polyester membrane (Dexter Corp. #9770) is laminated to the resulting adhesive film. This three layer assembly is peripherally heat sealed to Scotchpak backing #1009 forming transdermal patches. The reservoir of the patch is filled with a 24% (–) ketorolac tromethamine solution in 37% ethanol, 35% water, 1.1% isopropyl myristate and 0.4% hydroxy propyl cellulose. The opening in the heat seal by which the fill solution is introduced is sealed after filling.

What is claimed is:

1. A patch for the transdermal administration of ketorolac and through a patient's skin for a period of 12 hours or more, said patch comprising:
   (a) an occlusive backing layer having a skin-facing side, and
   (b) a drug depot having a skin-facing side and a skin-distal side in contact with said skin-facing side of said backing layer, said depot comprising,
      i. (–) ketorolac,
      ii. an enhancer combination comprising a plasticizing-type enhancer and a solvent-type enhancer, said plasticizing-type enhancer being a member selected from the group consisting of isopropyl myristate, caprylic triglyceride, capric triglyceride and glyceryl oleate, and said solvent-type enhancer being a member selected from the group consisting of propylene glycol, glycerin and butanol, and
      iii. an adhesive polymer in which said (–) ketorolac and said enhancer are dispersed,
   wherein said patch delivers (–) ketorolac through the skin facing side of said patch and through said patient's skin at a flux rate of about 20 g/cm$^2$.hr or more.

2. The patch of claim 1 having an active surface area of less than 30 cm$^2$.

3. The patch of claim 1 wherein said plasticizing-type enhancer is isopropyl myristate.

4. The patch of claim 1 wherein said solvent-type enhancer is propylene glycol.

5. A patch for the transdermal administration of ketorolac through a patient's skin for a period of 12 hours or more, said patch comprising:
   (a) an occlusive backing layer having a skin-facing side, and
   (b) a drug depot having a skin-facing side and a skin-distal side in contact with said skin-facing side of said backing layer, said depot comprising:
      i. (–) ketorolac,
      ii. an enhancer combination comprising a first portion of a plasticizing-type enhancer and a solvent-type enhancer, said plasticizing-type enhancer being a member selected from the group consisting of isopropyl myristate, caprylic triglyceride, capric triglyceride and glyceryl oleate, and said solvent-type enhancer being a member selected from the group consisting of ethanol, propanol and propylene glycol, and
      iii. polymer in which said (–) ketorolac and said enhancer are dispersed,
   (c) an adhesive layer comprising an adhesive and a second portion of said plasticizing-type enhancer, said adhesive layer in contact with said skin-facing side of said depot,
   wherein said patch delivers (–) ketorolac through the skin facing side of said patch and through said patient's skin at a flux rate of about 20 μg/cm$^2$.hr or more.

6. The patch of claim 5 having an active surface area of less than 30 cm$^2$.

7. The patch of claim 5 wherein said plasticizing-type enhancer is isopropyl myristate.

8. The patch of claim 5 wherein said solvent enhancer is ethanol.

9. The patch of claim 5 wherein said polymer is a hydrogel.

10. The patch of claim 5 further comprising:
    (d) a porous membrane having a skin-facing side and a skin-distal side in contact with said skin-facing side of said depot said membrane being permeable to said (–) ketorolac and said enhancer.

11. The patch of claim 10 wherein said porous membrane is a non-woven polyester.

12. A patch for the transdermal administration of ketorolac through a patient's skin for a period of 12 hours or more, said patch comprising:
    (a) an occlusive backing layer having a skin-facing side and a peripheral edge,
    (b) a drug depot having a skin-facing side and a skin-distal side in contact with said skin-facing side of said backing layer, said depot comprising:
       i. (–) ketorolac, and
       ii. an enhancer combination in which said (–) ketorolac is dispersed, said enhancer combination comprising a first portion of a plasticizing-type enhancer and a solvent-type enhancer, said plasticizing-type enhancer being a member selected from the group consisting of isopropyl myristate, caprylic triglyceride capric triglyceride and glyceryl oleate, and said solvent-type enhancer being a member selected from the group consisting of ethanol, propanol and propylene glycol,
    (c) a porous membrane permeable to said ketorolac and said enhancer, said membrane having a skin-facing side, a skin-distal side, and a peripheral edge, said skin-distal side of said membrane being in contact with said skin-facing side of said depot, and said peripheral edge of said membrane being sealed to said peripheral edge of said backing layer, and
    (d) an adhesive layer comprising an adhesive and a second portion of said plasticizing-type enhancer, said adhesive layer being in contact with said skin-facing side of said porous membrane,
    wherein said patch delivers (–) ketorolac through the skin facing side of said patch and through said patient's skin at a flux rate of about 20 μg/cm$^2$.hr or more.

13. The patch of claim 12 wherein said plasticizing-type enhancer is isopropyl myristate.

14. The patch of claim 12 wherein said solvent-type enhancer is ethanol.

15. The patch of claim 12 wherein said depot further comprises:
    iii. a foam material,
    said (–) ketorolac and said enhancer being contained in said foam material.

16. The patch of claim 12 wherein said porous membrane is a non-woven polyester.

17. A method of administering ketorolac to a patient in need of such administration, comprising:
 (a) applying to the skin of said patient a transdermal patch having a skin-facing side, said patch comprising:
  i. an occlusive backing layer having a skin-facing side, and
  ii. a drug depot having a skin-distal side in contact with said skin-facing side of said backing layer, said drug depot containing (−) ketorolac and an enhancer combination comprising a plasticizing-type enhancer and a solvent-type enhancer, said plasticizing-type enhancer being a member selected from the group consisting of isopropyl myristate, caprylic triglyceride, capric triglyceride and glyceryl oleate, and said solvent-type enhancer being a member selected from the group consisting of ethanol, propanol and propylene glycol, and
 (b) delivering (−) ketorolac through the skin facing side of said patch and through said patient's skin at a flux rate of about 20 μg/cm².hr or more.

18. The method of claim 17 wherein said patch has an active surface area of less than 30 cm².

19. The method of claim 17 wherein less than 30 mg of (−) ketorolac is delivered to said patient over a 24 hour period.

\* \* \* \* \*

UNITED STATES PATENT AND TRADEMARK OFFICE
CERTIFICATE OF CORRECTION

PATENT NO. : 5,589,498

DATED : December 31, 1996

INVENTOR(S) : Mohr et al.

It is certified that error appears in the above-identified patent and that said Letters Patent is hereby corrected as shown below:

Claim 1, column 13, line 34 should read-- $20 \mu g/cm^2 \cdot hr$ --.

Signed and Sealed this

Twenty-fifth Day of March, 1997

*Attest:*

BRUCE LEHMAN

*Attesting Officer*     *Commissioner of Patents and Trademarks*